United States Patent [19]

Gustilo et al.

[11] Patent Number: 4,950,298
[45] Date of Patent: Aug. 21, 1990

[54] MODULAR KNEE JOINT PROSTHESIS

[76] Inventors: Ramon B. Gustilo, 825 8th St. S., Minneapolis, Minn. 55404; James A. Rand, 200 SW. First St., Rochester, Minn. 55905; Jeffrey G. Roberts, 6248 Rockledge Dr., Bartlett, Tenn. 38134; Jennifer J. Lackey, 79 E. Lafayette Cir., Memphis, Tenn. 38111

[21] Appl. No.: 179,524

[22] Filed: Apr. 8, 1988

[51] Int. Cl.$^5$ .............................................. A61F 2/38
[52] U.S. Cl. ..................................................... 623/20
[58] Field of Search ........................ 623/16, 18, 20, 23

[56] References Cited

U.S. PATENT DOCUMENTS

| 4,209,861 | 7/1980 | Walker et al. | 623/20 |
| 4,213,209 | 7/1980 | Insall et al. | 623/20 |
| 4,298,992 | 11/1981 | Burstein et al. | 623/20 |
| 4,714,474 | 12/1987 | Brooks, Jr. et al. | 623/20 |
| 4,731,086 | 3/1988 | Whiteside et al. | 623/20 |

Primary Examiner—Richard J. Apley
Assistant Examiner—David J. Isabella
Attorney, Agent, or Firm—Pravel, Gambrell, Hewitt, Kimball & Krieger

[57] ABSTRACT

A femoral component base having a pair of laterally spaced apart condylar portions, each of which has an external surface that is smoothly convexly curved anterior-posteriorly to match generally the distal profile of the anatomical femoral condyle and smoothly convexly curved laterally throughout its antero-posterior extent. The external convexly curved surfaces engage the tibial component having a platform portion laterally with spaced apart concavities, each of which would receive one of the condylar portions of the femoral component to allow antero-posterior rotation between the components during use of the joint. The femoral component includes a modular member having adjustable plates for adjusting the position of the femoral component in response to the bone condition discovered during surgery. The tibial, femoral and modular components further include a triangular, ramp post and corresponding confined recess to limit flexion and undesirable lateral movement.

16 Claims, 3 Drawing Sheets

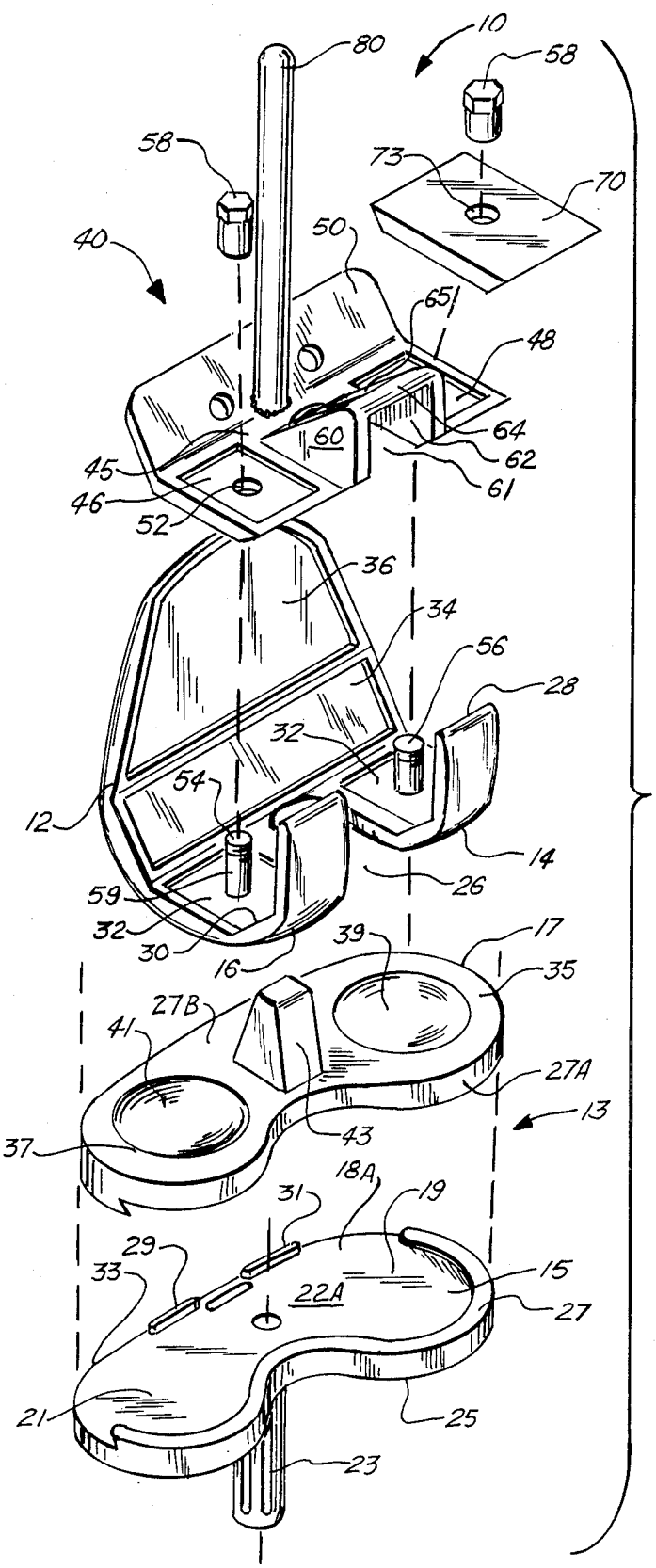
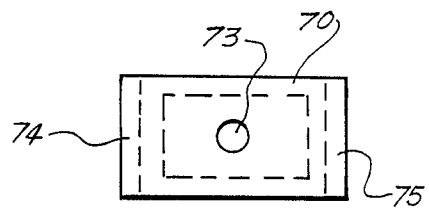
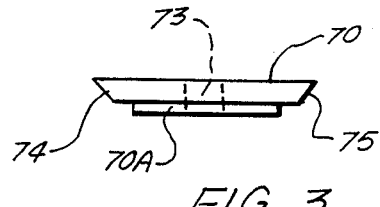
FIG. 1.
FIG. 2.
FIG. 3.

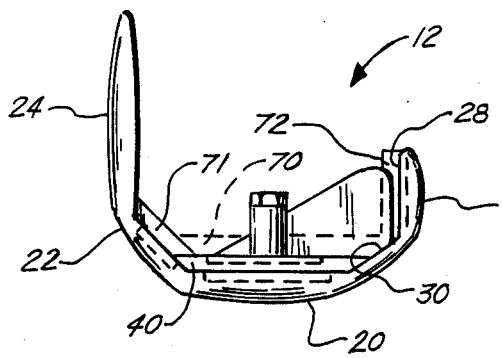
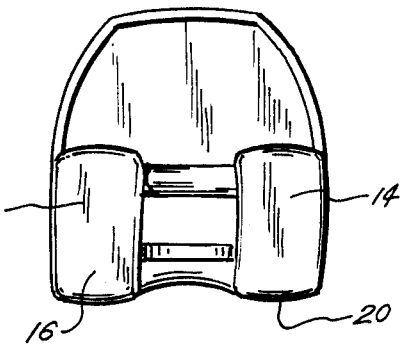
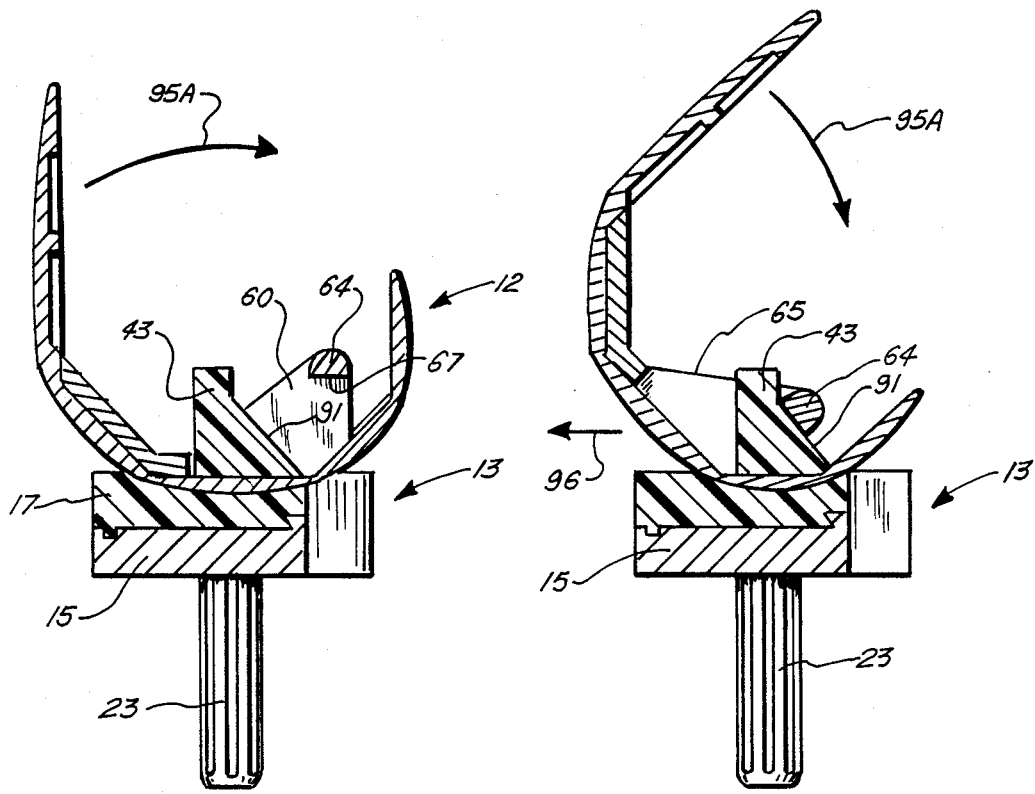

MODULAR KNEE JOINT PROSTHESIS

BACKGROUND OF THE INVENTION

1. Field of the Invention

The present invention relates to knee joint prostheses, and more particularly, to an implantable knee joint prosthesis including a primary femoral component of modular construction.

2. General Background

In the reconstruction of the anatomical knee joint by total replacement with a prosthetic joint, the femoral, tibial and patellar prosthetic components provide a total knee joint prosthesis in which the contacting surfaces of the components operate to provide a functioning knee joint. At the present time, most total knee prostheses provide for antero-posterior rotation in order to simulate movement similar to the anatomical knee joint with the tendons and ligaments of the joint imparting stability with the component affording a certain degree of stability in the medio-lateral movement. A very common type of knee joint presently utilized is disclosed in U.S. Pat. No. 4,298,992, issued on Nov. 10, 1981 for a "Posteriorly Stabilized Total Knee Joint Prosthesis" wherein there is included a femoral component utilizing a pair of laterally spaced apart condylar portions, each of which having an external surface convexly curved to match generally the lateral profile of the anatomical femoral condyle. U.S. Pat. No. 4,298,992 further discloses a tibial component and a platform portion including spaced apart concavities for receiving each of the condylar portions of the femoral component. The post extends from the tibial plateau into the intracondylar recess of the femoral component so that upon full flexion of the joint, the knee joint is stabilized between the tibial post and femoral recess. The '992 patent addresses the prevention of translocation of the knee during flexion.

During the surgical replacement of a total knee, the surgeon must conduct precise angulated cuts into the femoral condyles of the femur so as to position the femoral component snugly in place so that the joint operates smoothly and is able to undertake the various movements of an anatomical knee. In order to accommodate the femoral component precisely in place, the surgeon is confronted with the problem of having to cut away or "shave" bone that has been worn down or is in a weakened condition unknown to the surgeon until inspection of the bone during the course of the surgery. In order to properly mount the femoral component onto the femur, the weakened or worn portion of the bone must be removed, so that this component can be properly secured to solid bone. The result is that the surgeon may consequently, have to achieve a total knee replacement without having a means to replace greater bone loss than was originally foreseen, resulting in the undesirable condition that the particular leg is slightly shortened by the excessive cutting away of bone and that the location of the prosthetic knee is not precisely in line with the original anatomical knee.

SUMMARY OF THE PRESENT INVENTION

The present invention seeks to provide tibial and femoral components which would enable the surgeon to compensate for the excessive removal of bone through the use of the modular components that would be available to the surgeon during the surgery, the result being that the surgeon, although faced with loss of excessive bone, is able to construct the prosthetic knee to the exact position of the anatomical knee during the course of surgery. Further, the present invention allows rotational movement for the tibial and femoral components during flexion.

The apparatus of the present invention includes a femoral component having a pair of laterally spaced apart condylar portions, each of which has an external surface that is smoothly convexly curved antero-posteriorly to match generally the lateral profile of the anatomical femoral condyle. The external convexly curved surfaces engage laterally spaced apart concavities in the tibial component platform portion to allow antero-posterior rotation between the components during use of the joint. There is further provided a femoral platform positionable upon the inner surface of the femoral base portion, the femoral platform having a pair of laterally spaced apart portions, the undersurface of which registers with the surface of the femoral condyle, with each portion including interior parallel side walls, interconnected with a transverse intracondylar stabilizer bar, the pair of side walls defining an intracondylar recess which opens inferiorly toward the tibia, and for defining a passage through which the tibial post moves during flexion of the knee. There is further provided a pair of post members on the femoral base portion, each of which extends superiorly from the inner surface of each femoral condyle, for receiving the femoral platform, the post members accommodating threaded nuts thereupon to secure the platform in position within the femoral component while serving to secure the component to the femoral condyles. Further, the combination would include a plurality of interchangeable plate members positionable on the upper surface of the platform to increase the surface height of the platform once secured in position on the femoral component and a plurality of plate members positionable on the forward sloping wall of the base portion, the plate members once in position serving to provide a means to compensate for bone that has been worn away or cut away during surgery, so as to maintain the femoral component in relatively the same location as the anatomical femoral condyles.

Therefore, it is an object of the present invention to provide a knee prosthesis including a femoral component of modular construction;

It is still another object of the present invention to provide a total knee joint prosthesis wherein the femoral component may be constructed modularly to allow for replacement of the anatomical femoral condyle in relatively the same position as the anatomical femoral condyle; and It is still a further object of the present invention to provide a total knee joint prosthesis which includes a means for allowing stabilization of the knee joint as the knee joint is rotated and prevents subluxation of the femur relative to the tibia during flexion.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is an overall exploded view of the preferred embodiment of the apparatus of the present invention;

FIGS. 2 and 3 are plane and side elevational views of the modular plate members of the present invention;

FIGS. 7 and 8 are side elevational and top views respectively of a femoral component of the present invention; and FIGS. 9 and 10 are side cross-sectional views in generally schematic form showing the assembled components between full extension to substantially full flexion in the preferred embodiment of the apparatus of the present invention.

DETAILED DESCRIPTION OF THE PREFERRED EMBODIMENT

Figure 4:
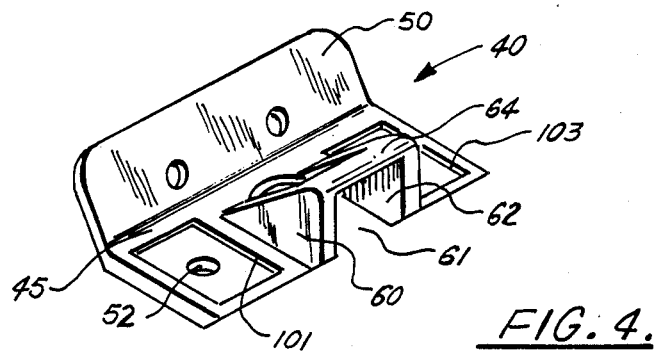
FIGS. 4 through 6 are perspective views of alternate embodiments of the platform portion of the apparatus of the present invention.

The preferred embodiment of the modular knee joint prosthesis is illustrated in the Figures by the numeral 10. Knee joint prosthesis 10 includes a primary femoral component 12, which is a modular component cooperating with a tibial component 13. The femoral component 12 is a generally U-shaped member as seen in a side view (FIG. 7); and comprises a pair of laterally spaced apart femoral condylar portions 14 and 16, each of which is smoothly convexly curved in lateral profile generally to match the curvature of the anatomical femoral condyle that is being replaced. Each condylar portion 14 and 16 is laterally convexly curved entirely along their antero-posterior extent. As seen in profile view in FIG. 7, each condyle 14 or 16 includes a posterior portion 18 which merges smoothly with the lower curved surface 20. Surface 20 is designed to register with the tibial base portion, which in turn merges smoothly with the convexly curved forward or anterior portion 22, the medial part of which is laterally concave to receive patella portion 24. The spaced apart femoral condylar portions 14 and 16 define a traveling space 26 therebetween for accommodating, during flexion, the movement of the tibial post, as will be described further. Further, the femoral component 12 is constructed along its interior surface so as to receive femoral platform 40 therewithin.

The component 12 includes a first pair of anterior faces 28, each respectively on the pair of femoral condylar components 14 and 16, leading to anterior angulated faces 30 and the lower base face 32 on each condylar component. The anterior portion 22 of femoral component 12 includes angulated face portion 34 joined to the base faces 32 and to an upper substantially vertical face 36, the various faces in the femoral component 12 defining an area for receiving the femoral platform 40 therewithin.

The tibial component 13 as seen in the FIGURES, would comprise a tibial base portion 15 for accommodating and affixing a tibial platform 17 thereupon. Tibial base portion 15 would include a floor portion 18A generally configured to resemble the overall configuration of the upper end portion of the tibia which is prepared to receive base portion 15 thereupon. Base portion 15 would include lateral and medial hemispheres 19 and 21 respectively, and include a flat superior surface 22A for receiving tibial platform 17 in engagement therewith. Further, base portion 15 would include a stabilizing post 23 extending from its inferior surface 25 of floor portion 18A, with stabilizing post 23 insertable into the tibial medullary canal and would provide for the stabilization of the component on the tibia. As seen further in the Figures, the preferred embodiment of the tibial component 13 would include a base portion 15, which would include a posterior raised wall 27 extending from substantially the medial outer wall to the lateral outer wall across the posterior edge of floor portion 18A, to serve as a means for engaging the posterior edge 27 of the tibial platform when the platform 17 is placed onto the base portion 15. Further, there is included a pair of anteriorly positioned raised walls 29 and 31 on the anterior edge 33 of base 15, so that edge 29 and 31 of base 15 would be engaged against the platform anterior wall 27B, and platform 17 secured in place between posterior wall 27 and anterior walls 29 and 31 and held rigidly in place. For purposes of construction, tibial component 13 could be a single piece component, and not include the separate platform 17 apart from the base portion 15.

Turning now to platform 17, platform 17 is shaped generally in the configuration of base portion 15, likewise having lateral and medial hemispheres 35 and 37 respectively, with hemispheres 35 and 37 each including a substantially oblong cavity 39 and 41 respectively, each of which would receive one of the femoral condylar portions 14 and 16 to be nested into the oblong cavities 39 and 41 so that anterior-posterior translation, lateral angulation and rotation are achieved, all of which would be involved in the normal articulation of the antomical knee joint.

As seen in the Figures, there is also included a central located stabilizer post 43 positioned on the superior face of tibial platform 17, the function of which will be described further. In the preferred embodiment, the radius of the posterior curvature of the component is slightly less than the radius of the lateral curvature of the femoral condylar portion so as to allow rotation therewithin.

Turning now to the modular component of the joint 12 as shown in FIG. 1, the femoral modular platform 40 includes a base portion 45 joined to a pair of spaced apart platform portions 46 and 48 to register with the inner faces 32 of the femoral condylar components 14 and 16. There is further provided an angulated member having anterior face 50 which would register against inner angled surface 34 of femoral component 12 as platform 40 is lowered onto femoral component 12. Each of the base portions 46 and 48 include a bore 52 for receiving therethrough pin members 54 and 56 which are mounted on condylar portions 14 and 16 and extend upwardly from surfaces 32. The pin members 54 and 56 are aligned with bores 52 to enable platform 40 to be secured therethrough via the use of mounting nuts 58 which threadably engage threads 59 of pin members 54 and 56. The mounting shaft 80 is attached to angled member 50 for mounting into the femur. As seen particularly in side view in FIG. 7, with the positioning of platform 40 onto femoral component 12, platform 40 provides a means for achieving a greater thickness to femoral component 12 to compensate for any excess loss of bone during the surgical procedure of implanting the component onto the anatomical femoral condyle. It should be noted also in FIG. 7 that the undersurface of platform 40 mates precisely with the angular configuration of the various inner surfaces 30, 32, and 34 of the femoral component to achieve a snug fit therebetween. However, for purposes of construction a cement which is standard in the industry could be utilized intermediate the platform 40 and femoral component 12 so as to further achieve a permanent fixture therebetween.

The modular platform 40 of the knee prosthesis 10 also includes additional modular components for achieving a construction of the femoral portion to meet unforeseen loss of bone during the course of surgery as described earlier. Turning now to FIGS. 1, 2 and 3, one type of modular component would include rectangular plates 70 which are positionable as seen in FIGS. 1 and 7 on the face portions 46 and 48 of platform 40. The plates 70 include a bore 73 for allowing pin members 56 and 54 to be secured therethrough as seen in the FIGURES. Therefore, in addition to the thickness of the initial platform 40 to compensate for bone loss, additional plates such as plate 70 may be affixed to the upper surfaces 46 and 48 of component 40 to provide a further height to the femoral component as indicated in phantom view in FIG. 7. It should be noted that in the construction of plate 70, plate 70 includes angulated front and rear faces 74 and 75 respectively, which register precisely with the sloped faces 30 and 50, respectively of femoral component 12 femoral platform 40 so as to achieve a firm and snug fit therebetween. The bottom of each adjustment plate 70 includes a rectangular raised area 70A for seating on surfaces 46 and 48. Again, for purposes of construction, cement may be positioned intermediate the components for achieving a more permanent fit therebetween.

As seen in FIG. 7, an additional plate 71 of similar construction to plate 70, may be positioned along the inner surface 50 of platform 40, so as to achieve a thickening of that particular area of the femoral component 12. Another plate 72 set along face 28 of component 12 cooperates with plates 70 and 71 again to compensate for loss of bone along that particular face as seen in FIG. 7. It is foreseen that the various types of plate members 70, 71, 72 utilized in this modular configuration, could be utilized along any inner face, i.e., any of the internal surfaces 28, 30, 32, and 34 enumerated in femoral base component 12, so as to provide means for allowing the replacement of loss of bone through a build-up of the condylar portion itself. Plate members 71 and 72, which are generally rectangular plates sized to fit against surfaces 34, 30, and 28 are similar to plate 70 except that no opening 73 or bottom insert portion 70A are needed, and would be secured to femoral platform 40 utilizing bone cement common in the art.

In addition, as seen in FIG. 1, platform 40 includes a fixation post or shaft member 80 which extends superiorly into the space within the femoral bone so as to further secure the entire femoral portion 12 to the femur. Fixation post 80 may be permanently positioned onto platform 40 as seen in FIG. 1, or platform 40 may be without a post 80, with the pair of mounting posts 54 and 56 providing the means for securing femoral portion 12 upon the femur, again with the assistance of cement. Various alternate embodiments of platform 40 will be discussed in detail further.

Returning to the construction of platform 40, there is further included a means generally designated as 100 for providing stability to the knee as the knee is flexed and a means to prevent lateral movement of the knee beyond a certain point which may result in dislocation of the joint. This means would include first and second triangulated vertical walls 60 and 62 which mount superiorly from the inner edge of the face portions 42 and 44, the walls 60 and 62 including a transverse stabilizing bar 64 interconnecting walls 60 and 62. The walls 60 and 62 have an angled edge or ramp 65 which extends from the highest point at transverse post member 64 at approximately a 45° angle to the base portion 45 of platform 40. The vertical walls 60 and 62 and angled edges 65 define a traveling space 61 therebetween for allowing travel of the tibial post 43 within space 61 during articulation of the knee, as will be described further.

Addressing an additional aspect of the present invention, reference is made to FIGS. 8 and 9 of the drawings. As just described, platform 40 includes the traveling, intercondylar space 61 defined by parallel triangulated wall portions 60 and 62 with horizontal stabilizing bar 64 spanning therebetween and angled top edges 65. As seen in the Figures, traveling space 61 serves as a means to provide tibial post 43 of tibial member 13 with a confined traveling space intermediate femoral condyles 14 and 16 when femoral condyles 14 and 16 are registered in recesses 39 and 41 to complete the construction of knee joint 10. Therefore, as seen in FIG. 9, femoral portion 12 is resting in tibia portion 13, when the knee is in full extension, such as a standing position, with the post 43 positioned intermediate triangulated walls 60 and 62 within space 61. As the knee is rotated in the direction of Arrow 95A, such as by raising the foot to the rear of the knee, the natural rotation of knee 10 would provide that femoral portion slide slightly forward in recesses 39 and 41. In order to prevent lateral movement to occur to the point where femoral portion would be disengaged from recesses 39 and 41 as seen in the direction of Arrow 96, transverse post member 64 would move from the position from its highest position as seen in FIG. 9 to a position where the lower face 67 of transverse bar 64 serves as a camming or limiting surface against the rear face 91 of tibial post 43. Upon transverse post 64 camming against face 91, femoral portion 12 is prevented from moving further forwardly than the position as seen in FIG. 10 although further rotation of the knee in the direction of Arrow 95A may occur. Therefore, transverse post 64 in cooperation with tibial post 43 serves to stabilize the knee as it is rotated to full flexion, i.e., from a 0° angle in FIG. 9 to substantially equal to or greater than 45+° angle during full flexion.

Lateral confinement of the knee is also provided by the cooperation of tibial ramp post 43 and the corresponding triangular or ramp recess formed by modular component walls 60 and 62. During rotation in a vertical plane, the post 43 rotates between extended portions rather freely. However, any undesirable or lateral or rotational movement of the knee is prevented by the enter-engagement of wall 91 of post 43 against triangular walls 60 and 62 forming travel recess 61 on the modular component 40.

Figure 5:
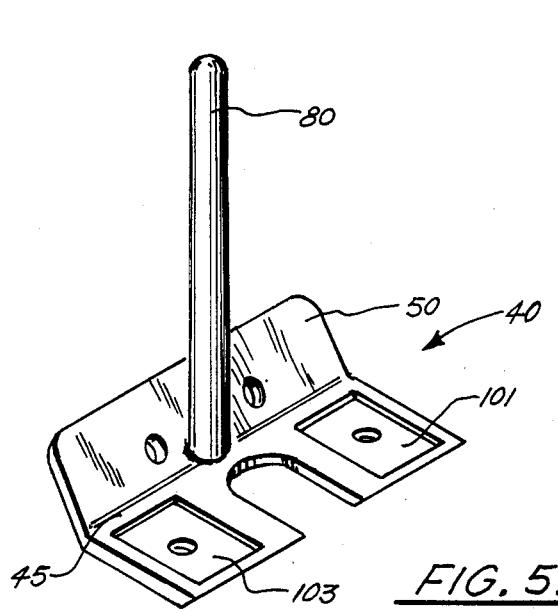
Figure 6:
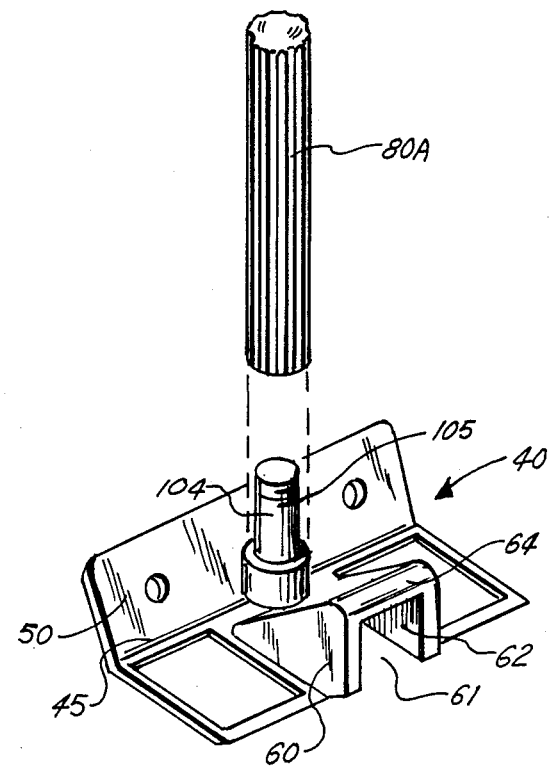

FIGS. 4 through 6 represent additional embodiments of platform portion 40, as is illustrated in FIG. 1 in the preferred embodiment. As seen in FIG. 4, platform portion 40, in this particular embodiment, would likewise include the lower base portion 45, the angulated base portion 50, and the centrally located traveling space 61 formed by triangular walls 60 and 62 and transverse connecting bar 64. Unlike the preferred embodiment, this particular embodiment would not include the post member 80 insertable into the femoral bone. In this particular embodiment, it is foreseen that the base 40 would be secured in position into femoral bone via the pair of mounting posts 54 and 56 which would protrude through bores 52 and would be secured onto femoral components 12 via nuts 58. It is foreseen that this particular embodiment would be used in a replacement knee which would not require the use of a central post 80 for purposes of function.

In FIG. 5, again there is illustrated platform 40 likewise including a base 45, angulated base portion 50, and in this embodiment, post member 80. Further, as illustrated, the platform 40 also contains rectangular recesses 101 and 103 respectively, for accommodating the rectangular inserts 70 as illustrated in FIGS. 2 and 3, for possibly building up the thickness of the component during use. The principal difference between this particular embodiment and the embodiment as illustrated in FIGS. 1 and 4, is the fact that this particular embodiment would be used on a tibial component which would not include the ramp post 43. Therefore, the centrally located process which provides posterior stabilization of the femoral component relative to the tibial component would not be utilized. Again, this embodiment would be used in a knee replacement which does not foresee the need to provide posterior stabilization between the femoral and the tibial components.

The embodiment in FIG. 6 is for the most part, identical to the principal embodiment as seen in the Figures, except for the fact that the embodiment in FIG. 6 would include an adaptor 104 positioned at the point where post 80 is positioned in the preferred embodiment, adaptor 104 including a truncated body member 105, cylindrical in shape, for accommodating a removable post 80A which would, for the most part, be frictionally engaged upon member 105 during use. Therefore, this particular embodiment rather than having a post affixedly attached to the base of platform 40, would have the adaptability to receive various lengths and diameter of posts depending on the need required for that particular insert. Structurally, however, it would resemble the principal embodiment in FIG. 1.

As was stated earlier, each of the embodiments, whether it be the preferred embodiment, or the embodiments illustrated in FIGS. 4 through 6 would all have the ability to receive the various inserts 70, 71, or 72 in order to build up the thickness of the femoral component once it is placed in position. In addition, although it is illustrated in the Figures that the inserts 70 are generally rectangular in nature, it is foreseen that the inserts could be of various thicknesses and sizes, so as to accommodate any particular loss of bone which would have to be replaced with the use of an insert during surgery.

In addition, although it is illustrated that the modular knee portion contain the platform 40 which may be attached to the inner surfaces of femoral component 12, it is possible that for purposes of construction platform 40 may be integral with femoral portion 12, and yet may however receive additional plate members 70, 71 or 72 in achieving greater thickness of the femoral component during implantation. Overall, it is foreseen that the modular nature of this invention would allow practically an unlimited application of construction members included in the basic construction so that a surgeon, when confronted with a problem of reconstruction during surgery, can solve that problem quite easily by substitution of lost bone with a modular plate member.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:
1. A knee joint prosthesis, comprising:
   (a) a tibial component comprising (i) an upwardly-facing bearing surface and (ii) means for fixedly connecting the tibial component to an exposed end of a tibia;
   (b) a femoral component comprising (i) a simulated condylar bearing surface for registering and cooperating with the bearing surface of the tibial component for simulating movement of the natural knee, and (ii) a femoral contact surface with pin means projecting therefrom for fixedly connecting the femoral component to an exposed end of a femur;
   (c) a femoral platform to be interposed between the femoral component and the exposed end of a femur, comprising (i) a base portion adapted to engage and register with the femoral contact surface and accommodate the pin means, and (ii) a central elongated fixation means dimensioned to be inserted in the canal with a length greater than the pin means to provide greater stabilization of the femoral component with respect to the femur for use in secondary implants.
2. The prosthesis of claim 1, wherein the simulated condylar bearing surface includes a pair of rounded condylar bearing portions separated by a space, the pin means including a fixation pin projecting from the femoral contact surface on both sides of the space.
3. The prosthesis of claim 1, wherein the elongated fixation means includes a support post projecting from the femoral platform and an elongated shaft member with an internal recess adapted to mate with the support post.
4. The prosthesis of claim 1, and further including stabilizing means on the femoral platform and a stabilizing post projecting from the bearing surface of the tibial component, the stabilizing post being shaped and positioned to engage the stabilizing means after the knee has been bent at a predetermined angle.
5. A knee joint prosthesis, comprising:
   (a) a tibial component comprising an upwardly-facing bearing surface and means for fixedly connecting the tibial component to an exposed end of a tibia;
   (b) a femoral component comprising (i) a simulated condylar bearing surface for registering and cooperating with the bearing surface of the tibial component for simulating movement of the natural knee, (ii) and a femoral contact surface with pin means projecting therefrom for fixedly connecting the femoral component to an exposed end of a femur;
   (c) the simulated condylar bearing surface including a pair of rounded condylar bearing portions separated by a space, the pin means including a fixation pin projecting from the femoral contact surface on both sides of the space;
   (d) a separate femoral platform to be interposed between the femoral component and the exposed end of a femur, comprising a base portion adapted to engage and register with the femoral contact surface; and
   (e) stabilizing means on the femoral platform and a stabilizing post projecting from the bearing surface of the tibial component, the stabilizing post being shaped and positioned to engage the stabilizing means after the knee has been bent at a predetermined angle.
6. The prosthesis of claim 1 or 5, wherein the stabilizing means includes a pair of walls on either side of the space separating the condylar bearing portions and a bar connecting the walls for engaging the stabilizing post.

7. The prosthesis of claim 1 or 5, wherein the femoral contact surface for each condylar bearing portion includes a recessed face defined by four side walls and a pin means projecting from each face.

8. The prosthesis of claim 1 or 5, wherein the base portion of the platform includes a femoral component contact face with a pair of contact surfaces that are substantial mirror images of the femoral contact surfaces, with openings therein through which the pin means can project.

9. The prosthesis of claim 1 or 5, wherein the pin means are threaded and further including a mounting nut for the pin means with internal threads sized to cooperate with the threads on the pin means.

10. The prosthesis of claim 1 or 5, wherein the platform has an upper side adapted to engage the exposed end of the femur shaped substantially identical to the femoral contact surface for each condylar bearing portion, the prosthesis further including a spacer with a contact surface sized and shaped to register with either the femoral contact surface for each condylar bearing portion or the upper side of the platform, the spacer also including at least one opening through which the pin means can project.

11. A modular knee system with interconnecting parts for adapting to various implant conditions, comprising:
  (a) a tibial component comprising (i) an interchangeable upwardly-facing bearing surface and (ii) means for fixedly connecting the tibial component to an exposed end of a tibia;
  (b) a femoral component comprising (i) a simulated condylar bearing surface for registering and cooperating with the bearing surface of the tibial component for simulating movement of the natural knee, and (ii) a femoral contact surface with pin means projecting therefrom for fixedly connecting the femoral component to an exposed end of a femur;
  (c) the simulated condylar bearing surface including a pair of rounded condylar bearing portions separated by a space, the pin means including fixation pins projecting from the femoral contact surface on both sides of the space;
  (d) a first femoral platform to be interposed between the femoral component and the exposed end of a femur, comprising (i) a base portion adapted to engage and register with the femoral contact surface, and (ii) an elongated fixation means with a length greater than the pin means to provide greater stabilization of the femoral component with respect to the femur for use in secondary implants;
  (e) a second femoral platform to be interposed between the femoral component and the exposed end of a femur, comprising (i) a base portion adapted to engage and register with the femoral contact surface, and (ii) stabilizing means being shaped and positioned to engage the stabilizing post after the knee has been bent a predetermined angle;
  (f) an upwardly-facing bearing surface for the tibial component including a stabilizing post projecting from the bearing surface of the tibial component, the stabilizing post being shaped and positioned to engage the stabilizing means after the knee has been bent a predetermined angle;
  (g) the first platform having an upper side adapted to engage the exposed end of the femur shaped identical to the femoral contact surface for each condylar bearing portion, the prosthesis further including a spacer with a contact surface sized and shaped to register with either the femoral contact surface for each condylar bearing portion or the upper side of the platform, the spacer also including at least one opening through which the fixation pin can project.

12. The knee system of claim 11, wherein the elongated fixation means includes a support post projecting from the femoral platform and an elongated shaft member with an internal recess adapted to mate with the support post.

13. The knee system of claim 11, wherein the stabilizing means includes a pair of walls on either side of the space separating the condylar bearing portions and a bar connecting the walls for engaging the stabilizing post.

14. The knee system of claim 11, wherein the femoral contact surface for each condylar bearing portion includes recessed face defined by four side walls and a pin means projecting from each face.

15. The knee system of claim 11, wherein the base portion of the platform includes a femoral component contact face with a pair of contact surfaces that are substantial mirror images of the femoral contact surfaces, with openings therein through which the pin means can project.

16. The knee system of claim 11, wherein the pin means is threaded and further including a mounting nut for the pin means with internal threads sized to cooperate with the threads on the pin means.

* * * * *